US005958907A

United States Patent [19]
Welsh

[11] Patent Number: 5,958,907
[45] Date of Patent: Sep. 28, 1999

[54] PHARMACEUTICAL COMPOSITIONS AND USES OF INORGANIC PYROPHOSPHATES

[75] Inventor: Michael J. Welsh, Riverside, Iowa

[73] Assignee: The University of Iowa Research Foundation, Iowa City, Iowa

[21] Appl. No.: 08/920,999

[22] Filed: Aug. 29, 1997

Related U.S. Application Data

[63] Continuation of application No. 08/484,847, Jun. 2, 1995, Pat. No. 5,686,114.

[51] Int. Cl.$^6$ ............................ A61K 31/66; A61K 33/42
[52] U.S. Cl. .......................... 514/108; 514/114; 514/851; 424/601
[58] Field of Search ............................ 424/601; 514/108, 514/114, 851

[56] References Cited

U.S. PATENT DOCUMENTS

| | | | |
|---|---|---|---|
| 5,407,661 | 4/1995 | Simone et al. | 424/49 |
| 5,686,114 | 11/1997 | Welsh | 424/601 |

OTHER PUBLICATIONS

Anderson, M.P. and M.J. Welsh (1992) "Regulation by ATP and ADP of CFTR Chloride Channels That Contain Mutant Nucleotide–Binding Domains" *Science* 257:1701–1704.

Anderson, M.P. et al. (1991) "Nucleoside Triphosphates Are Required to Open the CFTR Chloride Channel" *Cell* 67:775–784.

Bartels, E.M. et al. (1993) "The myosin molecule—charge response to nucleotide binding" *Biochem. Biophys. Acta* 1157:63–73.

Baukrowitz, T. et al. (1994) "Coupling of CFTR Cl$^-$ Channel Gating to an ATP Hydrolysis Cycle" *Neuron* 12:473–482.

Berger, H.A. et al. (1993) "Regulation of the Cystic Fibrosis Transmembrane Conductance Regulator Cl$^-$ Channel by Specific Protein Kinases and Protein Phosphatases" *J. Biol. Chem.* 268:2037–2047.

Bhalla, K. et al. (1985) "Isolation and Characterization of an Anthracycline–resistant Human Leukemic Cell Line" *Cancer Res.* 45:3657–3662.

Blobel, C.P. et al. (1992) "A potential fusion peptide and an integrin ligand domain in a protein active in sperm–egg fusion" *Nature* 356:248–251.

Busche, R. et al. (1989) "Equilibrium, kinetic and photoaffinity labeling studies of daunomycin binding to P–glycoprotein–containing membranes of multidrug–resistant Chinese hamster ovary cells" *Eur. J. Biochem.* 183:189–197.

Busche, R. et al. (1989) "Preparation and Utility of a Radioiodinated Analogue of Daunomycin in the Study of Multidrug Resistance" *Mol. Pharmacol.* 35:414–421.

Carson, M.R. et al. (1994) "Phosphate Stimulates CFTR Cl$^-$ Channels" *Biophys. J.* 67(5):1867–1875.

Chen, C.–J. et al. (1986) "Internal Duplication and Homology with Bacterial Transport Proteins in mdr1 (P–Glycoprotein) Gene from Multidrug–Resistant Human Cells" *Cell* 47:381–389.

Croop, J.M. et al. (1988) "Genetics of Multidrug Resistance" *J. Clin. Invest.* 81:1303–1309.

Cutting, G.R. et al. (1990) "A cluster of cystic fibrosis mutations in the first nucleotide–binding fold of the cystic fibrosis conductance regular protein" *Nature* 346:366–369.

Dalemans, W. et al. (1991) "Altered chloride ion channel kinetics associated with the F508 cystic fibrosis mutation" *Nature* 354:526–528.

Dean, M. et al. (1990) "Multiple Mutations in Highly Conserved Residues Are Found in Mildly Affected Cystic Fibrosis" *Cell* 61:863–870.

Denning, G.M. et al. (1992) "Processing of mutant cystic fibrosis transmembrane conductance regulator is temperature–sensitive" *Nature* 358:761–764.

Deverson, E.V. (1990) "MHC class II regions encoding proteins related to the multidrug resistance family of transmembrane transporters" *Nature* 348:738–740.

Endicott, J.A. and V. Ling (1989) "The Biochemistry of P–Glycoprotein–Mediated Multidrug Resistance" *Annu. Rev. Biochem.* 58:137–171.

Fleisch, H. et al. (1991) "Biophosphates: Pharmacology and Use in the Treatment of Tumour–Induced Hypercalcaemic and Metastatic Bone Disease" *Drugs* 42(6):919–944.

Frizzell, R.A. et al. (1986) "Altered Regulation of Airway Epithelial Cell Chloride Channels in Cystic Fibrosis" *Science* 233:558–560.

Goldfischer, S. et al. (1973) "Peroxisomal and Mitochondrial Defects in the Cerebro–Hepato–Renal Syndrome" *Science* 182:62–64.

Goldstein, L.J. et al. (1989) "Expression of a Multidrug Resistance Gene in Human Cancers" *J. Natl. Cancer Inst.* 81:116–124.

Gottesman and Pastan (1988) "The Multidrug Transporter, a Double–edged Sword" *J. Biol. Chem.* 263:12163–12166.

Greene, L.E. and E. Eisenberg (1980) "Dissociation of the Actin–Subfragment 1 Complex by Adenyl-5'-yl Imidodiphosphate, ADP, and PP$_i$" *J. Biol. Chem.* 255(2):543–548.

Gregory, R.J. et al. (1990) "Expression and characterization of the cystic fibrosis transmembrane conductance regulator" *Nature* 347:382–386.

Gros, P. et al. (1986) "Isolation and expression of a complementary DNA that confers multidrug resistance" *Nature* 323:728–731.

Gros, P. et al. (1986) "Mammalian Multidrug Resistance Gene: Complete cDNA Sequence Indicates Strong Homology to Bacterial Transport Proteins" *Cell* 47:371–380.

(List continued on next page.)

*Primary Examiner*—Kimberly Jordan
*Attorney, Agent, or Firm*—Foley Hoag & Eliot, LLP; Beth E. Arnold, Esq.; Diana M. Steel, D. Phil.

[57] ABSTRACT

Pharmaceutical compositions comprising an inorganic pyrophosphate (PPi) in a form that renders the PPi accessible to ABC proteins when administered to a subject in vivo, as well as use of the compositions for treating subjects having a disease or disorder associated with inappropriate or inadequate ABC protein activity (e.g., cystic fibrosis, multi drug resistance, Zellweger's Syndrome) is disclosed.

11 Claims, 2 Drawing Sheets

Gunderson, K.L. et al. (1994) "Effects of Pyrophosphate and Nucleotide Analogs Suggest a Role for ATP Hydrolysis in Cystic Fibrosis Transmembrane Regulator Channel Grating" *J. Biol. Chem.* 269(30):19349–19353.

Hamada, H. and T. Tsuruo (1988) "Purification of the 170– to 180–Kilodalton Membrane Glycoprotein Associated with Multidrug Resistance" *J. Biol. Chem.* 263:1454–1458.

Hartman, J. et al. (1992) "Recombinant Synthesis, Purification, and Nucleotide Binding Characteristics of the First Nucleotide Binding Domain of the Cystic Fibrosis Gene Product" *J. Biol. Chem.* 267:6455–6458.

Hwang, T.–C. et al. (1989) "Cl⁻ Channels in CF: Lack of Activation by Protein Kinase C and cAMP–Dependent Protein Kinase" *Science* 244:1351–1353.

Hwang, T.–C. et al. (1994) "Regulation of the gating of cystic fibrosis transmembrane conductance regulator C1 channels by phosphorylation and ATP hydrolysis" *PNAS USA* 91:4698–4702.

Hyde, S.C. et al. (1990) "Structural model of ATP–binding proteins associated with cystic fibrosis, multidrug resistance and bacterial transport" *Nature* 346:362–365.

Imanaka, T. et al. (1987) "Translocation of Acyl–CoA Oxidase into Peroxisomes Requires ATP Hydrolysis but Not a Membrane Potential" *J. Cell Biol.* 105(6 Part 2):2915–2922.

Issartel, J.–P. et al. (1987) "Is Pyrophosphate an Analog of Adenosine Disphosphate for Beef Heart Mitochondrial $F_1$–ATPase" *J. Biol. Chem.* 262:13538–13544.

Kamijo, K. et al. (1990) "The 70–kDa Peroxisomal Membrane Protein Is a Member of the Mdr (P–glycoprotein)–related ATP–binding Protein Superfamily" *J. Biol. Chem.* 265(8):4534–4540.

Kerem, B.–S. et al. (1989) "Identification of the Cystic Fibrosis Gene: Genetic Analysis" *Science* 245:1073–1080.

Kerem, B.–S. et al. (1990) "Identification of mutations in regions corresponding to the two putative nucleotide (ATP)–binding folds of the cystic fibrosis gene" *PNAS USA* 87:8447–8451.

Knowles, M.R. et al. (1991) "Activation by Extracellular Nucleotides of Chloride Secretion in the Airway Epithelia of Patients with Cystic Fibrosis" *N. Eng. J. Med.* 325(8):533–538.

Knowles, M.R. et al. (1990) "A Pilot Study of Aerosolized Amiloride for the Treatment of Lung Disease in Cystic Fibrosis" *N. Eng. J. Med.* 322(17):1189–1194.

Ko, Y.H. et al. (1994) "The Cystic Fibrosis Transmembrane Conductance Regulator" *J. Biol. Chem.* 269:14584–14588.

Kuchler, K. et al. (1989) "*Saccharomyces cerevisiae* STE6 gene product: a novel pathway for protein export in eukaryotic cells" *EMBO J.* 8(13):3973–3984.

Li, M. et al. (1988) "Cyclic AMP–dependent protein kinase opens chloride channels in normal but not cystic fibrosis airway epithelium" *Nature* 331:358–360.

Marshall, S.E. et al. (1990) "Selection and Evaluation of Recipients for Heart–Lung and Lung Transplantation" *Chest* 98: 1488–1494.

McElvaney, N.G. et al. (1991) "Aerosol 1–antitrysin treatment for cystic fibrosis" *The Lancet* 337:392–394.

Michel, L. et al. (1989) "Synthesis and Properties of Azidonitrophenyl Pyrophosphate, a Photoaffinity Probe of Nucleotide Binding Sites of Mitochondrial $F_1$ –ATPase" *Biochem.* 28:10022–10028.

Monaco, J.J. et al. (1990) "Transport Protein Genes in Murine MHC: Possible Implications for Antigen Processing" *Science* 250:1723–1726.

Nagel, G. et al. (1992) "The protein kinase A–regulated cardiac Cl⁻ channel resembles the cystic fibrosis transmembrane conductance regulator" *Nature* 360:81–84.

Peinnequin, A. et al. (1992) "Does Pyrophosphate Bind to the Catalytic Sites of Mitochondrial $F_1$–ATPase?" *Biochem.* 31(7):2088–2092.

Quinton, P.M. (1990) "Cystic fibrosis: a disease in electrolyte transport" *FASEB J.* 4:2709–2717.

Reiner, M. et al. (1975) "Le traitment de la maladie de Paget par les diphosphonates (Treatment of Paget's Disease with Phosphonates)" *Schweiz. Med. Wschr.* 105(50):1701–1703.

Rich, D.P. et al. (1990) "Expression of cystic fibrosis transmembrane conductance regulator corrects defective chloride channel regulation in cystic fibrosis airway epithelial cells" *Nature* 347:358–362.

Riordan, J.R. (1993) "The Cystic Fibrosis Transmembrane Conductance Regulator" *Ann. Rev. Physiol* 55:609–630.

Riordan, J.R. et al. (1989) "Identification of the Cystic Fibrosis Gene: Cloning and Characterization of Complementary DNA" *Science* 245:1066–1073.

Rommens, J.M. et al. (1989) "Identification of the Cystic Fibrosis Gene: Chromosome Walking and Jumping" *Science* 245:1059–1065.

Santos, M.J. et al. (1988) "Peroxisomal Membrane Ghosts in Zellweger Syndrome–Aberrant Organelle Assembly" *Science* 239:1536–1538.

Schutgens, R.B.H. et al. (1986) "Peroxisomal disorders: A newly recognised group of genetic diseases" *Eur. J. Pediatr.* 144:430–440.

Shak, S. et al. (1990) "Recombinant human DNase I reduces the viscosity of cystic fibrosis sputum" *PNAS USA* 87:9188–9192.

Sheppard, D.N. et al. (1993) "Mutations in CFTR associated with mild–disease–form Cl⁻ channels with altered pore properties" *Nature* 362:160–164.

Spies, T. et al. (1990) "A gene in the human major histocompatibility complex class II region controlling the class I antigen presentation pathway" *Nature* 348:744–747.

Spies, T. and R. DeMars (1991) "Restored expression of major histocompatibility complex class I molecules by gene transfer of a putative peptide transporter" *Nature* 351:323–324.

Thiebuat, F. et al. (1987) "Cellular localization of the multidrug–resistance gene product P–glycoprotein in normal human tissues" *PNAS USA* 84:7735–7738.

Thomas P.J. et al. (1992) "The Cystic Fibrosis Transmembrane Conductance Regulator" *J. Biol. Chem.* 267(9):5727–5730.

Travis, S.M. et al. (1993) "Interaction of Nucleotides with Membrane–associated Cystic Fibrosis Transmembrane Conductance Regulator" *J. Biol. Chem.* 268:15336–15339.

Trezise, A.E.O. et al. (1992) "The multidrug resistance and cystic fibrosis genes habe complementary patterns of epithelial expression" *EMBO J.* 11(12):4291–4303.

Tsui, L.–C. (1992) "The Spectrum of Cystic Fibrosis Mutations" *Trends in Genetics* 8(11):392–398.

Valverde, M.A. et al. (1992) "Volume–regulated chloride channels associated with the human multidrug–resistance P–glycoprotein" *Nature* 355:830–833.

Veeze, H.J. et al. (1994) "Determinants of Mild Clinical Symptoms in Cystic Fibrosis Patients" *J. Clin. Invest.* 93:461–466.

Wang, H.–Y. et al. (1989) "Site–directed Anti–peptide Antibodies Define the Topography of the—Adrenergic Receptor" *J. Biol. Chem.* 264:14424–14431.

Welsh, M.J. and C.M. Liedtke (1986) "Chloride and potassium channels in cystic fibrosis airway epithelia" *Nature* 322:467–470.

Welsh, M.J. and A.E. Smith (1993) "Molecular Mechanisms of CFTR Chloride Channel Dysfunction in Cystic Fibrosis" *Cell* 73:1251–1254.

Welsh, M.J. et al. (1992) "Cystic Fibrosis Transmembrane Conductance Regulator: A Chloride Channel with Novel Regulation" *Neuron* 8:821–829.

Winter, M.C. et al. (1994) "Effect of ATP Concentration on CFTR $C^-$ Channels: A Kinetic Analysis of Channel Regulation" *Biophys J.* 66:1398–1403.

Wittes, R.E. and A. Golden (1986) "Unresolved Issues in Combination Chemotherapy" *Cancer Treat. Rep.* 70(1):105–125.

Yount, R.G. et al. (1971) "Adenylyl Imidodiphosphate, an Adenosine Triphosphate Analog Containing a P–N–P Linkage" *Biochem.* 10(13):2484–2489.

PHARMACEUTICAL COMPOSITIONS AND USES OF INORGANIC PYROPHOSPHATES

This application is a continuation of Ser. No. 08/484,847, filed Jun. 2, 1995 now U.S. Pat. No. 5,686,114.

BACKGROUND OF THE INVENTION

ATP-binding cassette (ABC) proteins are an ancient class of membrane transporters, found throughout phylogeny in eubacteria, archezoa and metakaryota (Gros. P. et al. (1986) Cell 47:371–370; Chen, C. J. et al. (1986) Cell 47:381–389; Kuchler, K. et al. (1989) EMBO J. 8:3973–3984; Riordan, J. R. et al. (1989) Science 245:1066–1073; Hyde, S. et al. (1990) Nature 346:362–365). During evolution, ABC proteins have become specialized in uptake and secretion, intracellular transport, cell detoxification and signaling and translocate highly diverse compounds across cell membranes, such as ions, amphiphiles, sugars, peptides and proteins.

The diverse functions and substrate specificities are accomplished by a common protein architecture (Hyde, S. et al. (1990) Nature 346:362–365). Each of the 1–4 functional units of an ABC protein consists of a hydrophobic domain of six membrane spanning segments and a hydrophilic cytoplasmic domain which is able to bind ATP. Three 20–45 amino acid sequence motifs in the nucleotide binding folds (NBFs) are highly conserved among ABC transporters.

The ABC protein family includes yeast (STE6 gene product), bacterial (haemolysin transport protein; hisP, malK, oppD and pstB proteins which are involved in ATP-dependent transport of specific molecules through bacterial inner cell membrane) and mammalian proteins. Four mammalian family members are currently known (PMP70, MHC-linked transport protein, P-glycoprotein, and the cystic fibrosis transmembrane conductance regulator protein (CFTR)).

PMP70

The peroxisomal membrane protein (PMP70) is one of the major integral membrane proteins of rat liver peroxisomes (Kamijo, K. et al. (1990) J. Biol. Chem. 265(8):4534–4540). It is believed that PMP70 may be involved in an active transport process through the peroxisomal membrane. One of the proposed functions for PMP70 protein is the transport of acyl-CoA compounds across peroxisomal membrane. Peroxisomes are cellular organelles bounded by a single membrane, and are observed in almost all types of eucaryotic cells. Although the physiological significance of peroxisomes has remained elusive, diseases caused by a general dysfunction of peroxisomes, including Zellweger syndrome, infantile Refsum disease, hyperpipecolic acidaemia, and neonatal adrenoleukodystrophy, have recently been recognized (Schutgens, R. B. H. et al. (1986) Eur. J Pediatr. 144:430–440). The severe clinical manifestation of these diseases indicate the indispensable roles of mammalian peroxisomes.

In cells of patients with Zellweger syndrome, peroxisomes are morphologically absent (Goldfischer, S. et al. (1973) Science 182:62–64). Biogenesis of peroxisomes is apparently impaired in this disorder; the cause may be defects in the protein machinery of the peroxisomes (Santos, M. J. et al. (1988) Science 239:1536–1538). It has been further postulated that the primary biochemical lesion is at the level of the biosynthesis of a protein essential for the import of peroxisomal enzymes from the cytoplasm into the peroxisomes which utilizes adenosine triphosphate during import (Schutgens et al. (1986) Eur. J. Pediatr. 144:430–440; Imanaka, T. (1987) J. Cell Biol. 105:2915).

MHC-linked (TAP) Transport Proteins

The MHC-linked (TAP) transport proteins appear to be required for antigen processing and presentation (Deverson, E. V. (1990) Nature 348:738–740; Monaco, J. J. et al. (1990) Science 250:1723–1726; Spies, T. et al., (1990) Nature 348:744–747). This MHC-linked transport protein may deliver intracellularly degraded antigens to the endoplasmic reticulum for binding to the class I major histocompatability molecules (Spies and DeMars (1991) Nature 351:323–324). Several mutant cell lines have been described in the literature, human B lymphoblastoid cell line (LCL) mutant and mutant murine cell line RMA-S, which have lost the ability to form peptide-MHC complexes. Since antigen that is derived from the cytoplasm must cross a lipid bilayer in order to associate with the external portion of MHC class I molecules, the most likely defect in these cells may be an inability to translocate the antigen from the cytoplasm into the appropriate membrane bound compartment where this association normally takes place. The region of the MHC implicated in these mutations contains the genes for the MHC-linked transport protein.

P-glycoprotein

P-glycoprotein is primarily expressed at epithelial and endothelial surfaces (Thiebaut, F. et al., (1987) PNAS USA 84:7735–7738) and is assumed to play an essential role in absorption and/or secretion. P-glycoprotein is believed to have two distinct and independent functions. P-glycoprotein is an active transporter which pumps hydrophobic drugs out of cells, reducing their cytoplasmic concentration and therefore toxicity. Thus, one function of P-glycoprotein is to eliminate toxic metabolites or xenobiotic compounds from the body (Endicott and Ling (1989) Annu. Rev. Biochem. 58:137–171; Croop, J. M. et al. (1988) J. Clin. Invest. 81:1303–1309; Gottesman and Pastan (1988) J. Biol. Chem. 263:12163–12166; Van der Bliek and Borst (1989) Adv. Cancer Res. 52:165–203).

P-glycoprotein has also been associated with a volume-regulated chloride channel activity. It has been reported that expression of P-glycoprotein generates volumneregulated, ATP-dependent, chloride-sensitive channels, with properties similar to channels characterized previously in epithelial cells (Valverde, M. A. (1992) Nature 355:830–8330). Therefore, P-glycoprotein is also believed to be involved in nutrient absorption in intestinal villus or in the placental cells at the site of material-foetal exchange (Trezise, A. E. O. (1992) EMBO J. 11(12):4291–4303). Unlike CFTR channels which are regulated by cyclic, P-glycoprotein is volume regulated, (e.g., swelling induced activation).

Overexpression of P-glycoprotein confers the phenotype of multidrug resistance (mdr; Gros, P. et al. (1986) Nature 323:728–731) which may cause failure of chemotherapy in cancer (Goldstein, L. J. et al. (1989) J. Natl. Cancer Inst. 81:116–124). The selection and proliferation of drug-resistant tumor cells represents a major cause of failure in the chemotherapeutic treatment of human tumors. Tumors initially sensitive to a cytotoxic agent often recur and are resistant to a broad spectrum of chemotherapeutic drugs (Wittes and Golden (1986) Cancer Treat. Rep. 70:105–125). From the study of highly drug-resistant cell lines derived in vitro, it is generally agreed that a net decrease of the intracellular concentration of drug underlies the multidrug-resistant phenotype (Bhalla, K. et al. (1985) Cancer Res. 45:3657–3662). It is now believed that P-glycoprotein binds the drugs to which a mdr cell is resistant or collaterally sensitive (Busche, R. et al. (1989) Mol. Pharmacol. 35:414–421; Busche, R. et al. (1989) Eur. J. Biochem.

183:189–197) and hydrolyzes ATP (Hamada and Tsuruo (1988) *J. Biol. Chem* 263:1454–1458).

Cystic Fibrosis Transmembrane Conductance Regulator protein (CFTR)

The cystic fibrosis transmembrane conductance Regulator protein (CFTR) is a 1480 amino acid protein containing two membrane-spanning domains (MSDs), two nucleotide binding domains (NBDs) and a unique R domain, that functions as a chloride channel regulated by phosphorylation and by nucleoside triphosphates.

Cystic Fibrosis (CF) is the most common fatal genetic disease in humans (Welsh M. J. et al. in The Metabolic Basis of Inherited Diseases, Vol. III, pp. 3799–3876 (Scriver, C. R. et al. eds., McGraw-Hill, New York (1995)). Approximately one in every 2,500 infants in the United States is born with the disease. At the present time, there are approximately 30,000 CF patients in the United States. Despite current standard therapy, the median age of survival is only 26 years. Disease of the pulmonary airways is the major cause of morbidity and is responsible for 95% of the mortality. The first manifestation of lung disease is often a cough, followed by progressive dyspnea. Tenacious sputum becomes purulent due to colonization of bacteria. Chronic bronchitis and bronchiectasis can be partially treated with the current therapy, but the course is punctuated by increasingly frequent exacerbations of the pulmonary disease. As the disease progresses, the patient's activity is progressively limited. End-stage lung disease is heralded by increasing hypoxemia, pulmonary hypertension, and cor pulmonale.

The upper airways of the nose and sinuses are also involved by CF. Most patients develop chronic sinusitis. Nasal polyps occur in 15–20% of patients and are common by the second decade of life. Gastrointestinal problems are also frequent in CF; infants may suffer meconium ileus. Exocrine pancreatic insufficiency, which produces symptoms of malabsorption, is present in the large majority of patients with CF. Males are almost uniformly infertile and fertility is decreased in females.

Based on both genetic and molecular analyses, a gene associated with CF was isolated as part of 21 individual cDNA clones and its protein product predicted (Kerem, B. S. et al. (1989) *Science* 245:1073–1080; Riordan, J. R. et al. (1989) *Science* 245:1066–1073; Rommens, J. M. et al. (1989) *Science* 245:1059–1065)). European patent application publication number: 0 446 017 A1 describes the construction of the gene into a continuous strand, expression of the gene as a functional protein and confirmation that mutations of the gene are responsible for CF. (See also Gregory, R. J. et al. (1990) *Nature* 347:382–386; Rich, D. P. et al. (1990) *Nature* 347:358–362).

The protein product of the CF associated gene is called the cystic fibrosis transmembrane conductance regulator (CFTR) (Riordan, J. R. et al. (1989) *Science* 245:1066–1073). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan, J. R. et al. (1989) *Science* 245:1066–1073; Hyde, S. C. et al. (1990) *Nature* 346:362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. R. et al. (1989) *Science* 245:1066–1073; Frizzell, R. A. et al. (1986) *Science* 233:558–560; Welsh, M. J. and Liedtke, C. M. (1986) *Nature* 322:467; Li, M. et al. (1988) *Nature* 311:358–360; Hwang, T-C. et al. (1989) *Science* 244:1351–1353; Anderson, M. P. and Welsh, M. J. (1992) *Science* 257:1701–1704.

Sequence analysis of the CFTR gene of CF chromosomes has revealed a variety of disease causing mutations (Cutting, G. R. et al. (1990) *Nature* 346:366–369; Dean, M. et al. (1990) *Cell* 61:863:870; and Kerem, B-S. et al. (1989) *Science* 245:1073–1080; Kerem, B-S et al. (1990) *Proc. Natl. Acad. Sci. USA* 87:8447–8451). Population studies have indicated that the most common CF mutation, a deletion of the 3 nucleotides that encode phenylalanine at position 508 of the CFTR amino acid sequence ($\Delta$F508), is associated with approximately 70% of the cases of cystic fibrosis. This mutation results in the failure of an epithelial cell chloride channel to respond to cAMP (Welsh and Smith (1993) *Cell* 73:1251–1254). In airway cells, this leads to an imbalance in ion and fluid transport. It is widely believed that this causes abnormal mucus secretion, and ultimately results in pulmonary infection and epithelial cell damage. In addition to the processing defect, the function of CFTR-$\Delta$F508 is decreased as indicated by a reduced $P_O$ (Dalemans, W. et al. (1991) *Nature* 354:526–528; Denning, G. M. et al. (1992) *Nature* 358:761–764). G551S, a mutation in NBD1, is correctly processed but has altered ATP-dependent channel regulation resulting in a reduced $P_O$ (Anderson, M. P. and Welsh, M. J. (1992) *Science* 257:1701–1704). R 117H, which contains a mutation in the membrane-spanning domain, is also correctly processed, but has altered ion conducting properties producing an overall decrease in function (Sheppard, D. N. et al. (1993) *Nature* 362:160–164).

To date, the primary objectives of treatment for CF have been to control infection, promote mucus clearance, and improve nutrition (Welsh M. J. et al. in The Metabolic Basis of Inherited Diseases, Vol. III, pp. 3799–3876 (Scriver, C. R. et al. eds., McGraw-Hill, New York (1995)). Intensive antibiotic use and a program of postural drainage with chest percussion are the mainstays of therapy. However, as the disease progresses, frequent hospitalizations are required. Nutritional regimens include pancreatic enzymes and fat-soluble vitamins. Bronchodilators are used at times. Corticosteroids have been used to reduce inflammation, but they may produce significant adverse effects and their benefits are not certain. In extreme cases, lung transplantation is sometimes attempted (Marshall, S. et al. (1990) *Chest* 98:1488).

Most efforts to develop new therapies for CF have focused on the pulmonary complications. Because CF mucus consists of a high concentration of DNA, derived from lysed neutrophils, one approach has been to develop recombinant human DNase (Shak, S. et al. (1990) *Proc. Natl. Sci. Acad USA* 87:9188). Preliminary reports suggest that aerosolized enzyme may be effective in reducing the viscosity of mucus. This could be helpful in clearing the airways of obstruction and perhaps in reducing infections. In an attempt to limit damage caused by an excess of neutrophil derived elastase, protease inhibitors have been tested. For example, alpha-1-antitrypsin purified from human plasma has been aerosolized to deliver enzyme activity to lungs of CF patients (McElvaney, N. et al. (1991) *The Lancet* 337:392). Another approach would be the use of agents to inhibit the action of oxidants derived from neutrophils. Although biochemical parameters have been successfully measured, the long term beneficial effects of these treatments have not been established.

Based on knowledge of the cystic fibrosis gene, three general corrective approaches (as opposed to therapies aimed at ameliorating the symptoms) are currently being pursued to reverse the abnormally decreased chloride secretion and increased sodium absorption in CF airways. Defective electrolyte transport by airway epithelia is thought to alter the composition of the respiratory secretions and mucus (Welsh M. J. et al. in The Metabolic Basis of Inherited Diseases, Vol. III, pp. 3799–3876 (Scriver, C. R. et al. eds., McGraw-Hill, New York (1995); Quinton, P. M. (1990) *FASEB J.* 4:2709–2717). Hence, pharmacological treatments aimed at correcting the abnormalities in electrolyte transport are being pursued. Trials are in progress with aerosolized versions of the drug amiloride; a diuretic that inhibits sodium channels, thereby inhibiting sodium absorption. Initial results indicate that the drug is safe and suggest a slight change in the rate of disease progression, as measured by lung function tests (Knowles, M. et al. (1990) *N. Eng.J.Med.* 322:1189–1194; App, E. (1990) *Am. Rev. Respir. Dis.* 141–605.) Nucleotides, such as ATP or UTP, stimulate purinergic receptors in the airway epithelium. As a result, they open a class of chloride channel that is different from CFTR chloride channels. In vitro studies indicate that ATP and UTP can stimulate chloride secretion (Knowles, M. et al. (1991) *N. Eng. J. Med.* 325–533). Preliminary trials to test the ability of nucleotides to stimulate secretion in vivo, and thereby correct the electrolyte transport abnormalities are underway.

As with all pharmacological agents, issues such as drug toxicity and dosing will be important in developing an appropriate pharmacological agent for treating CF. A more fundamental consideration with pharmacological approaches to CF therapy is whether the chloride channel activity associated with CFTR is the crucial property that leads to the disease state. The CFTR is an epithelial Cl⁻ channel with novel structure and regulation (Welsh, M. J. et al. (1992) *Neuron* 8:821–829; Riordan, J. R. (1993) *Annu. Rev. Physiol.* 55:609–630). CFTR is composed of two membrane spanning domains which contribute to formation of the ion conducting pore and three cytoplasmic domains that regulate channel activity: Two nucleotide binding domains (NBDs), and the R domain. The presence of two NBDs confer a complex and poorly understood mechanism of regulation on channel activity. Phosphorylation of the R domain by cAMP-dependent protein kinase (PKA) is necessary, but not sufficient, for channel activity. Once the R domain has been phosphorylated, the NBDs must bind (Anderson, M. P. and Welsh, M. J. (1992) *Science* 257:1701–1704; Thomas, P. J. et al. (1992) *J. Biol. Chem.* 267:5727–5730; Ko, Y. H. et al. (1994) *J. Biol. Chem.* 269:14584–14588; Hartman, J. et al. (1992) *J. Biol. Chem.* 267:6455–6458; Travis, S. M. et al. (1993) *J. Biol. Chem.* 268:15336–15339) and probably hydrolyze (Anderson, M. P. and Welsh, M. J. (1992) *Science* 257:1701–1704; Hwang, T. C. et al. (1994) *PNAS USA* 91:4698–4702; Baukrowitz, T. et al. (1994) *Neuron* 12:473–482; Nagel, G. et al. (1992) *Neuron* 360:81–84) ATP in order to open. In addition, ATP hydrolysis may be required to close the channel (Hwang, T. C. et al. (1994) *PNAS USA* 91:4698–4702; Baukrowitz, T. et al. (1994) *Neuron* 12:473–482). Studies of the CFTR containing site-directed mutations suggest that the two NBDs do not have equivalent functions in channel regulation (Anderson, M. P. and Welsh, M. J. (1992) *Science* 257:1701–1704), and it has been proposed previously that hydrolysis of ATP at NBD1 opens the channel, while hydrolysis of ATP at NBD2 regulates closure. An important goal of CF research is to understand the function of CFTR and to use that knowledge to develop better treatments for the disease.

A second approach to curing cystic fibrosis, "protein replacement" seeks to deliver functional, recombinant CFTR to CF mutant cells to directly augment the missing CFTR activity. The concept of protein replacement therapy for CF is simple: a preparation of highly purified recombinant CFTR formulated in some fusogenic liposome or reassembled virus carrier delivered to the airways by instillation or aerosol. However, attempts at formulating a CF protein replacement therapeutic have met with difficulties. For example, CFTR is not a soluble protein of the type that has been used for previous protein replacement therapies or for other therapeutic uses. There may be a limit to the amount of a membrane protein with biochemical activity that can be expressed in a recombinant cell. There are reports in the literature of $10^5$–$10^6$ molecules/cell representing the upper limit (Wang, H. Y. et. al. (1989) *J. Biol. Chem* 264:14424), compared to 2000 molecules /second/cell being reported for secreted proteins such as EPO, insulin, growth hormone, and tPA.

In addition to limited expression capabilities, the purification of CFTR, a membrane bound protein, is more difficult than purification of a soluble protein. Membrane proteins require solubilization in detergents. However, purification of CFTR in the presence of detergents represent a less efficient process than the purification process required of soluble proteins. Other potential obstacles to a protein replacement approach include: 1) the inaccessibility of airway epithelium caused by mucus build-up and the hostile nature of the environment in CF airways; 2) potential immunogenicity ; and 3) the fusion of CFTR with recipient cells may be inefficient.

A third approach to cystic fibrosis treatment is a gene therapy approach in which DNA encoding CFTR is transferred to CF defective cells (e.g. of the respiratory tract). However, methods to introduce DNA into cells are generally inefficient. Since viruses have evolved very efficient means to introduce their nucleic acid into cells, many approaches to gene therapy make use of engineered defective viruses. However, viral vectors have limited space for accommodating foreign genes. For example, adeno-associated virus (AAV) although an attractive gene therapy vector in many respects, has only 4.5 Kb available for exogenous DNA. DNA encoding the full length CFTR gene represents the upper limit. Gene therapy approaches to CF will face many of the same clinical challenges as protein therapy.

Although there has been notable progress in developing curative therapies for CF based on knowledge of the gene encoding CFTR, the expressed protein product and mechanism of action, there are obstacles confronting every approach. New approaches for treating CF and other diseases or conditions associated inadequate or inappropriate function of ATP-binding cassette (ABC) proteins are needed.

SUMMARY OF THE INVENTION

The present invention is based on the discovery that inorganic pyrophosphates or their analogs can alter the activity of ATP-binding cassette (ABC) proteins. As a result of this finding, the instant invention provides new compositions and therapies for treating diseases or conditions associated with inappropriate or inadequate activity of ABC proteins, particularly mammalian ABC proteins, such as the cystic fibrosis transmembrane conductance regulator protein (CFTR), P-glycoprotein, MHC-linked transport protein or peroxisomal membrane protein.

In one aspect, the instant invention features pharmaceutical compositions of inorganic pyrophosphate (PPi) in a form that renders the PPi accessible to ABC proteins when administered to a subject in vivo. In preferred embodiments, the pharmaceutical composition of PPi include a delivery vehicle (e.g. a liposome, virosome or microsome) or is chemically modified to increase hydrophobicity and allow partitioning though the lipid membrane of cells. The PPi can be in a form which is hydrolyzable or non-hydrolyzable (e.g., etidronate disodium, immidophosphate (PNP) or methylenediphosphonic acid (PCP)). In addition, the pharmaceutical composition is preferably of a dose effective for altering the activity of an ATP-binding cassette (ABC) protein.

In another aspect, the invention features methods for treating or preventing a disease or condition associated with inappropriate or inadequate ABC protein activity in a subject by administering to the subject an effective amount of an inorganic pyrophosphate. In a preferred embodiment, the subject is a mammal and the ABC protein is selected from the group consisting of: CFTR, P-glycoprotein, MHC-linked transport protein or peroxisomal membrane protein. In one embodiment, the invention features methods for treating Cystic Fibrosis in a patient comprising administering to the patient an effective amount of an inorganic pyrophosphate. In another embodiment, the invention features methods for treating infantile Refsum disease, hyperpipecolic acidaemia, neonatal adrenoleukodystrophy or Zellweger's Syndrome.

Inorganic pyrophosphates are small molecules that can be taken orally. In addition, since in vivo administration of certain PPi compositions for treating tumor-induced bone disease is unassociated with side effects, the pharmaceuticals should be safe.

DESCRIPTION OF THE DRAWINGS

FIG. 1 is a graph showing the effect of inorganic pyrophosphate ($PP_i$) on kinetically modeled rate constants. A. A linear three state model of CFTR channel activity composed of two closed states ($C_1$ and $C_2$), one open state (O), and four rate constants ($\beta_1$, $\beta_2$, $\alpha_1$, and $\alpha_2$). Panels B–E show values of rate constants before and after addition of 5 mM $PP_i$. Rate constants were derived as described in the following examples from four experiments in which the membrane patch contained only one active channel, studied in the presence of 0.3 mM ATP and 75 nM PKA. Asterisks indicate $p<0.05$.

FIG. 2 is a schematic diagram presenting a model showing the control of the nucleotide binding domain (NBD) and adenosine triphosphate (ATP) over CFTR gating. Panel A shows the effect of ATP on the gating of phosphorylated CFTR channels; panel B shows the effect of ATP plus $PP_i$. In each panel events at the two NBDs and corresponding channel gating (far right in each panel) are indicated from top to bottom.

DETAILED DESCRIPTION OF THE INVENTION

The instant invention is based on the surprising finding that the administration of inorganic pyrophosphate or a non-hydrolyzable inorganic pyrophosphate analog can stimulate the activity of a mutant or wild-type CFTR Cl⁻ channel in the presence of ATP. Based on this finding, the invention features methods for treating or preventing a disease or condition associated with inappropriate or inadequate ABC protein activity.

Pharmaceutical Compositions

As used herein, the term "inorganic pyrophosphate (PPi)" refers to an inorganic ion consisting of two phosphate groups joined by a phosphate-phosphate high energy bond. The term is intended to include hydrolyzable inorganic pyrophosphates and non-hydrolyzable analogs. Examples of non-hydrolyzable inorganic pyrophosphate compounds include etidronate disodium, immidophosphate (PNP) or methylenediphosphonic acid (PCP), which are all commercially available.

Certain non-hydrolyzable inorganic pyrophosphate compounds are currently administered to treat tumor-induced bone disease (Fleich et al. (1991) *Drugs* 42(6):919–944). Although the effective dose is still a matter of debate, one slow infusion of 600 mg of PCP or 500 mg/day etidronate for 3 days have shown efficacy. Administrations are to be repeated if calcaemia does not decrease satisfactorily after a few days or when the effect subsides and blood calcium starts to rise again. It has also been reported that calcaemia can be maintained after initial treatment by a daily oral administration of 1600 mg PCP.

Because ABC transporter proteins are membrane proteins, preferable PPi pharmaceutical compositions are in a form that facilitates contact with and/or uptake by cell membranes. For example, PPi compounds can be chemically modified to increase their hydrophobicity and allow partitioning though the lipid membrane of cells. For example, a chemical modification that is routinely used is an addition of phosphoesters to the charged oxygens of the inorganic pyrophosphate. This modification neutralizes the charge of the inorganic pyrophosphate and increases its hydrophobicity. By increasing the size of the phosphoester used (e.g., methyl, ethyl or t-butyl esters), the level of hydrophobicity can be increased. Phosphoester groups are easily hydrolyzed once they enter the cell, so that a phosphoester modification should not interfere with the ability of inorganic pyrophosphates to bind to ABC transporter proteins.

Alternatively, inorganic pyrophosphate compositions can be administered in conjunction with a delivery vehicle. As used herein, the term "delivery vehicle" refers to any hydrophobic moiety, which is useful for transferring hydrophilic inorganic pyrophosphates across the lipid membrane of a cell and into the cell cytosol where they can interact with ABC proteins. Examples of appropriate hydrophobic moieties for use in the invention include detergent or other amphipathic molecule micelles, membrane vesicles, liposomes, virosomes, and microsomes. Preferred hydrophobic moieties are naturally fusogenic or can be engineered to become fusogenic (e.g., by destabilizing lipid bilayers or endocytosis). Fusion proteins can be obtained from viruses such as parainfluenza viruses 1–3, respiratory syncytial virus (RSV), influenza A, Sendai virus, and togavirus fusion protein. Nonviral fusion proteins include normal cellular proteins that mediate cell-cell fusion. Other nonviral fusion proteins include the sperm protein PH-30 which is an integral membrane protein located on the surface of sperm cells that is believed to mediate fusion between the sperm and the egg. (See e.g., Blobel et al. (1992) *Nature* 356:248–251). Still other nonviral fusion proteins include chimaeric PH-30 proteins such as PH-30 and the binding component of hemaglutinin from influenza virus and PH-30 and a disintegrin (e.g. bitistatin, barbourin, kistrin, and echistatin). In addition, lipid membranes can be fused using traditional chemical fusogens such as polyethylene glycol (PEG).

Inorganic pyrophosphate compounds alone or optionally in conjunction with a delivery vehicle can be admixed with a pharmaceutically acceptable carrier and administered to a subject in need. A "pharmaceutically acceptable carrier" as used herein refers to a material that can be co-administered with an inorganic pyrophosphate and which allows the inorganic pyrophosphate to perform its intended function (e.g., alter the activity of ABC proteins). Examples of such carriers include solvents, dispersion media, delay agents. The use of such media and agents for pharmaceutically active substances is well known in the art. Any conventional media and agent compatible with the inorganic pyrophosphate can serve as a pharmaceutically acceptable carrier for use in the subject invention.

Therapeutic Uses of the Pharmaceutical Compositions

CFTR-Based Diseases or Conditions

As described in further detail in the following Examples, inorganic pyrophosphates (PPis) have been shown to stimulate mutant CFTR Cl⁻ channels by 2 or 3 fold, as evidenced by an increase in ion (e.g. chloride ion) transport across cellular membranes. PPi stimulates mutant CFTR Cl⁻ channel by binding to the nucleotide binding domain (NBD) in the presence of ATP. This stimulation induces a significant change in net function, thereby alleviating the severity of the disease. Hydrolysis of PPi is not required for stimulation since hydrolyzable and non-hydrolyzable forms of PPi were equally effective.

Present data suggest that very little CFTR function is required to prevent disease or attenuate its severity. Individuals who have only 8–10% of normal CFTR transcripts maintain normal airways function (Chu, C. S. et al. (1992) *J. Clin. Invest.* 90:785–790). In addition, CFTR mutants which retain partial Cl⁻ channel activity are associated with a milder clinical phenotype (Sheppard, D. N. et al. (1993) *Nature* 362:160–164). Individuals with residual agonist-induced Cl⁻ secretion tend to have milder clinical symptoms and a later age at diagnosis (Veeze, H. J. et al. (1994) *J. Clin. Invest.* 93:461–466). Thus if $PP_i$ increased the activity of mutant CFTR by 2 or 3 fold (as shown in the Example below), it is possible that it could produce a significant change in net function and might alter the severity of the disease.

It is possible that interaction of PPi with the NBD of CFTR improves the processing of mutant CFTR. For example, it is known that CFTR ΔF508 has defective processing. An interaction with PPi might change the conformation or the volting and thereby allow the mutant ΔF508 protein to escape from the endoplasmic reticulum and be delivered to the plasma membrane.

In addition, the data presented in the following Example provides evidence that PPi can stimulate wild-type (i.e. non-mutant) CFTR. CFTR is known to be important in fluid and electrolyte secretion by the intestine. Therefore stimulation of CFTR by PPi could be useful for non-CF patients, who suffer from constipation or other electrolyte or fluid disorders.

Since PPi has been found to bind to CFTR's nucleotide binding domains (NBD) and NBDs are highly conserved among the ABC family of transporters, PPi should interact with other ABC proteins, particularly other mammalian ABC proteins, such as PMP70s, MHC-linked (TAP) transport proteins, and P-glycoproteins, potentially resulting in a therapeutic effect.

PMP70- Based Diseases or Conditions

Peroxisomes are cytoplasmic organelles containing enzymes for the production and decomposition of hydrogen peroxide. Peroxisomes are thought to be involved in oxidative processes in vivo and dysfunctional peroxisomes are thought to be involved in infantile Refsum disease, hyperpipecolic acidaemia and neonatal adrenoleukodystrophy.

Peroxisomes are morphologically absent in cells of patients with Zellweger syndrome (Goldfischer, S. et al. (1973) *Science* 182:62–64). Biogenesis of peroxisomes is apparently impaired in this disorder caused by defective protein machinery (Santos, M. J. et al. (1988) *Science* 239:1536–1538). It has been further postulated that the primary biochemical lesion is at the level of the biosynthesis of a protein essential for the import of peroxisomal enzymes from the cytoplasm into the peroxisomes which utilizes adenosine triphosphate during import (Schutgens et al. (1986) *Eur. J Pediatr.* 144:430–440; Imanaka, T. (1987) *J. Cell Biol.* 105:2915). If the lesion resulting in Zellweger's Syndrome or in another peroxisome-based disease is in the biosynthesis of the PMP70 protein, pharmaceutical compositions of the present invention would be useful in potentiating the activity of existing PMP70 proteins, so that they can compensate for the reduced synthesis and thus alleviate disease phenotypes.

MHC-linked (TAP) transport protein- Based Diseases or Conditions

TAP proteins are involved with transporting peptides into the endoplasmic reticulum of cells where they interact with Class I molecules. TAP transporters are therefore important in antigen presentation. The work described in the following Example suggests that non-hydrolyzable PPi compositions will interact with the NBD of MHC-linked (TAP) transport proteins, preventing hydrolysis and thereby inhibiting function.

The interaction of non-hydrolyzable PPi analogs with a TAP transport protein, blocking antigen presentation by the human leukocyte antigen (HLA) system suggests a number of therapeutic uses. For example, in vivo administration of PPi should be of use in treating an autoimmune disease, by preventing presentation of antigens that are the basis of autoimmunity. Furthermore, administration of inorganic pyrophosphate analogs could be of value in prevention of organ transplant rejection. For example, the transplanted organ may present antigen to the postimmune system thereby producing rejection. Inhibition of TAP transporters via administration of inorganic pyrophosphate analogs could prevent or ameliorate this effect. In addition, the binding of non-hydrolyzable inorganic pyrophosphates to TAP transporters can minimize recognition of any foreign protein by the host immune system. For example, non-hydrolyzable PPi could be administered in conjunction with gene therapy vectors to prevent an immune response to the vectors by a subject.

P-glycoprotein-based Diseases or Conditions

Analogous to bacterial ABC transporters, P-glycoprotein has been postulated to function as an energy-requiring drug-efflux pump. P-glycoprotein is also thought to be involved with nutrient absorption, particularly from the intestine. Overexpression of P-glycoprotein confers the phenotype of multidrug resistance (mdr), which may cause chemotherapies (e.g. against cancer or infection) to fail. It is thought that P-glycoprotein binds the drugs to which a mdr cell is resistant or collaterally sensitive.

The binding of non-hydrolyzable pyrophosphate compounds to the NBD of P-glycoproteins should inhibit the activity of P-glycoprotein by preventing hydrolysis. As a result it would useful to adminster non-hydrolyzable pyrophosphate compounds in conjunction with chemotherapies.

For therapy, a PPi pharmaceutical composition can be administered to a "subject", which is preferably a mammal (e.g., a mammal such as a human, dog, cat, horse, cow, goat, rat or mouse), by any route that allows the inorganic pyrophosphate to perform its intended function. Examples of routes of administration which can be used include injection (subcutaneous, intravenous, parenterally, intraperitoneally, etc.), oral, inhalation (via an aerosol), transdermal, and rectal. A preferred route of administration is by inhalation (e.g., of an aerosolized pharmaceutical composition). In addition, prior to administration, it may be useful to administer agents to clear obstructions to target cells. For example, it may be useful to remove mucus (e.g. by administering DNAse) prior to administering an aerosolized PPi pharmaceutical composition to the lungs of a CF patient.

Depending on the route of administration, the lipid vesicle can be coated with or in a material to protect it from the natural conditions which may detrimentally effect its ability to perform its intended function.- Dosage regimes may be adjusted for purposes of improving the therapeutic response to the membrane-associated protein of the lipid vesicle. For example, several divided doses may be administered daily or the dose may be proportionally reduced as indicated by the exigencies of the therapeutic situation.

An "effective amount" of inorganic pyrophosphate is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, the selected route for administration of the agent, and the type of CF mutation. Over 200 different varieties of CF mutation have been identified to date, e.g., $\Delta$F508, R117H, or G551S (see for example Tsui, L-C (1992) "The Spectrum of Cystic Fibrosis Mutations" Trends in Genetics 8 (11) 329–398), some are associated with more severe symptoms than others. The determination of appropriate "effective amounts" is within the ordinary skill of the art.

The present invention is further illustrated by the following example which in no way should be construed as limiting the invention. The contents of all cited references (including literature references, issued patents, published patent applications, and co-pending patent applications) cited throughout this application are hereby expressly incorporated by reference.

Example The effect of PPi and PPi analogs on the CFTR Cl⁻ channel activity

Materials and Methods (i) Chemicals and Solutions

Sodium pyrophosphate (PPi) was obtained from EM Science, Gibbstown, N.J. Catalytic subunit of PKA was from Promega Corp., Madison Wis. Methylenediphosphonic acid (PCP, trisodium salt tetrahydrate) was obtained from Aldrich Chemical Co., Milwaukee, Wis. Etidronate disodium (1-hydroxyethylidenebisphosphonic acid, Didronel, 300 mg/6 ml $H_2O$), was obtained from Pharma, Minneapolis, Minn. Adenosine 5'-triphosphate (ATP; disodium salt), imidodiphosphate (PNP, sodium salt), and all other reagents were obtained from Sigma Chemical Co., St. Louis, Mo.

For experiments with excised inside-out membrane patches, the pipette (extracellular) solution contained (in mM): 140 NMDG (N-methyl-D-glucamine), 100 aspartic acid, 35.5 HCI, S CaCl2, 2 MgCl2, 10 HEPES (4-[2-hydroxyethyl]-1-piperazine ethanesulfonic acid), pH 7.3 with 1 N NaOH. bath (intracellular) solution contained (in mM): 140 NMDG, 135.5 HCI, 3 MgCl2, 10 HEPES, 4 Cs and 1 EGTA, pH 7.3 with 1 N HCl ([Ca2+]free<10-8 M). PPi and PPi analog stock solutions were 200 mM in CsEGTA-free bath solution, pH 7.3, and diluted to desired final concentration in bath solution, except for etidronate disodium, which was diluted from commercial preparation. For Ussing chamber experiments, the mucosal (apical) solution contained (in mM): 135 NaCl, 1.2 MgCl2, 1.2 CaCl2, 2.4 K2HPO4, 0.6 KH2PO4, and 10 HEPES, pH 7.3. The submucosal (basolateral) solution contained (in mM): 135 Na gluconate, 7 mM MgSO4, 2.4 K2HP04, 0.6 KH2PO4, 10 HEPES, 10 dextrose, no added calcium, and 1 MgATP, pH 7.3.

(ii) Cells and Transfection Procedure

For patch clamp experiments, three different cell types expressing wild-type and mutant CFTR were used: stably transfected C127 mouse mammary epithelia cells, NIH 3T3 fibroblasts, or transiently transfected HeLa cells. Transient transfection of HeLa cells with the vaccinia virus/bacteriophage T7 hybrid expression system was as previously described (Fuerst, T. R. et al. (1986) *PNAS USA* 83:8122–8126; Carson, M. R. and Welsh, M. J. (1993) *Am. J. Physiol.* 265:L27–L3). Similar results were obtained with all cell types, and the data are combined. For experiments with $\Delta$F508 CFTR, stably transfected cells were incubated at 25 C. for 12–72 h prior to use (Denning, G. M. et al. (1992) *Nature* 358; 761–764). For experiment with polarized T-84 intestinal epithelial monolayers, cells were plated at a density of $5 \times 10^5$ cells/cm² on permeable filter supports (Millicell HA filters, Millipore, Bedford, Mass., 0.4 $\mu$m pore size, 27 mM diameter). Transepithelial resistance was monitored with a EVOM epithelial voltohmmeter (World Precision Instruments, Sarasota, Fla.), and filters with resistances between 4 to 7 k$\Omega$ were used.

(iii) Patch-clamp Technique

Methods for excised, inside-out patch-clamp recording are similar to those previously described (Carson, M. R. and Welsh, M. J. (1993) *Am. J. Physiol.* 265:L27–L32; Hamill, O. P. et al. (1981) *Pfluegers Arch.* 391;85–100; Anderson, M. P. et al. (1991) *Cell* 67:775–784). An Axopatch 200 amplifier (Axon Instruments, Inc., Foster City), was used for voltage-clamping and current amplification. A microcomputer and the pClamp software package (Axon Instruments, Inc.) were used for data acquisition and analysis. Data were recorded on videotape following pulse code modulation using a PCM-2 AID VCR adapter (Medical Systems Corporation, Greenvale, N.Y.). Patch pipettes were fabricated as described (Carson, M. R. and Welsh, M. J. (1993) *Am. J. Physiol.* 265:L27–L32), with pipette resistances of 5 to 15 M$\Omega$, and with seal resistance routinely greater than 5 G$\Omega$. Voltages are referenced to the extracellular side of the membrane. Excised macro-patch experiments were performed at a holding potential of −40 or −80 mV; single channel data were recorded at a holding potential of −80 mV. Experiments were conducted at 34–36° C. using a temperature-controlled microscope stage (Brook Industries, Lake Villa, Ill.).

For excised macro-patch data, replayed records were filtered at 1 kHz using a variable 8-pole Bessel filter (Frequency Devices Inc., Haverhill, Mass.) and digitized at 2 kHz. Each time course data point represents the average current from 1 s with one data point collected every 5 s. Average currents for an intervention were determined as the average of the last 12 data points (the last min) during the intervention. To compensate for any channel run-down during an experiment, specific interventions were bracketed when possible with current measurements made with similar concentrations of ATP but without the test compound; the intervention current was then compared to the average of pre- and post-intervention currents. For single channel analysis, replayed data were filtered at 1 kHz using a variable 8-pole Bessel filter, digitized at 5 kHz, and digitally filtered at 500 Hz. Idealized records were created using a half-height transition protocol; transitions less than 1 ms in duration were not included in the analysis. For the purpose of illustration, time-course figures are inverted so that an upward deflection represents an inward current, data points during solution perfusion were not included in some figures, and single channel traces were digitally filtered at 200 Hz.

Burst analysis was performed as previously described (Carson, M. R. et al. (1994) *Biophys. J.* (In Press)), using a $t_c$ (the time which separates interburst closures from intraburst closures) of 20 ms. This value was derived from analysis of wild-type CFTR closed-time histograms derived from excised inside-out membrane patches containing a single channel studied in the presence of 1 mM ATP plus PKA, and by the method of Sigurdson et al.. (Sigurdson, W. J. et al. (1987) *J. Exp. Biol.* 127:191–209). Closures longer than 20 ms were considered to define interburst closures, while closures shorter than this time were considered gaps within bursts. Burst data for PPi, PNP, and PCP were derived from experiments in which the membrane patch contained one active channel. For experiments with etidronate and ΔF508 CFTR, burst data were from patches containing four or fewer active channels; bursts in which there were no superimposed openings and which were separated from other bursts by greater than 20 ms were included in the analysis. It has been previously shown that no discernible bias is observed by including burst data from patches with more than one channel.

(iv) Maximum Likelihood Analysis and Kinetic Modeling

Maximum likelihood analysis and kinetic modeling were performed as described (Winter, M. C. et al. (1994) *Biophys. J.* 66:1398–1403). Briefly, unfiltered single channel data were digitized on a microcomputer (Apple Macintosh, Apple Computer, Inc., Cupertine, Calif.) equipped with a multifunctional data acquisition board (NB-MIO-16) and LabVIEW 2 software (National Instruments, Austin, Tex.) at 5 kHz following filtering with an 8-pole Bessel filter (Frequency Devices Inc., Haverhill, Mass.) at a corner frequency of 1 kHz with subsequent digital filtering at 500 Hz. Previous work has shown that a linear three state model ($C_1 \leftrightarrow C_2 \leftrightarrow O$) best describes the kinetics of CFTR channel activity (Winter, M. C. et al. (1994) *Biophys. J.* 66:1398–1403). The Maple 5 symbolic algebra program (Waterloo Maple Software, Waterloo, Canada) was used to derive the open and closed time probability density functions for this model by solving the matrix equations in terms of the rate constants. The resulting equations were used in LabVIEW 2 to determine the set of rate constants which yielded the maximum likelihood for the open and closed times observed with different experimental interventions.

(v) [α—$^{32}$P]8-N3ATP Photolabeling

Photolabeling of membrane-associated CFTR was performed as previously described (Travis, S. M. et al. (1993) *J. Biol. Chem.* 268:15336–15339). Monolayer cultures of Spodoptera frugiperda (Sf9) cells were infected with a baculovirus containing the entire coding sequence for human CFTR (gift of R. J. Gregory and A. E. Smith, Genzyme Corp., Framingham, Mass.). Membranes were prepared by differential centrifugation and resuspended in 20 mM HEPES, pH 7.5, 50 mM NaCl, 3 mM MgSO4, with 2 μg/ml each of leupeptin, aprotinin, and pepstatin. Membrane-associated CFTR was phosphorylated prior to photolabeling by incubation with 100 nM PKA and 0.1 mM ATP in buffer containing 10 m MgCl2 and 50 mM 1,4-piperazine diethane sulfonic acid, pH 6.8 for 20 min at 30° C., then diluted in 12 volumes buffer containing 20 mM tris(hydroxymethyl)aminomethane, pH 7.5, 0.2 mM EGTA and 1 μM calyculin A. Membranes were collected by centrifugation and resuspended at a concentration of 2.5 mg protein/ml in the same buffer.

Photolabeling was performed by preincubating membranes (50 μg membrane protein/sample) on ice with [α-$^{32}$P] 8-N3ATP (30 αM, 6–12 Ci/mmol) and PPi (in mM). After 60 s UV irradiation, CFTR was solubilized and immunoprecipitated as described (Travis, S. M. et al. (1993) *J. Biol. Chem.* 268:15336–15339) using antibodies raised against the R domain (M13-1, 0.3 μg/sample) and against the C terminus (M1-4, 10 μg/sample). Immunocomplexes were analyzed by SDS-PAGE and incorporation of [α-$^{32}$P]8-N3ATP was quantitated with an AMBIS radioanalytic imaging system (AMBIS Systems, Inc., San Diego, Calif.). Data are expressed as percent of radiolabel incorporation relative to control which had no added PPi.

(vi) Measurement of Apical Membrane Cl$^-$ Current

Apical membrane Cl$^-$ current was measured as previously described (Ostedgaard, L. S. et al. (1992) *Am. J. Physiol.* 263:L104–L112). T-84 monolayers with resistances between 4–7 kΩ were mounted in modified Ussing chambers (Jim's Instruments, Iowa City, Iowa), and the basolateral membrane was permeabilized by addition of approximately 100 μg/ml S. aureus α-toxin to the serosal solution. S. aureus α-toxin produces pores in the basolateral membrane which are large enough to allow passage of ions and small molecules such as nucleotides, without permitting exchange of larger proteins and cellular constituents (Ostedgaard, L. S. et al. (1992) *Am. J. Physiol.* 263:L104–L112; Fussle, R. et al. (1981) *J. Cell Biol.* 91:83–94). Permeabilization was confirmed by both a transient current upon addition of toxin which returned to baseline, as well as by stimulation of short circuit current by addition of 10 μM cAMP, which is cell impermeant in the absence of permeabilization. Data are expressed as current observed five min after the intervention.

Results are means ± SEM of n observations. Statistical significance was assessed using a paired, unpaired, or one population Student's t-test as appropriate.

RESULTS (i) Pyrophosphate Stimulates CFTR Cl$^-$ Current

To determine if inorganic pyrophosphate ($PP_i$) would alter CFTR Cl$^-$ channel activity, 5 mM $PP_i$ was added to an excised, inside-out membrane patch containing many CFTR channels which had been phosphorylated by PKA. It was shown that addition of 5 mM $PP_i$ in the presence of 0.3 mM ATP produced a reversible increase in Cl$^-$ current. Addition of $PP_i$ in the absence of ATP did not stimulate current, suggesting that $PP_i$ alone cannot open CFTR Cl$^-$ channels or substitute for ATP in supporting activity. Furthermore, as the concentration of $PP_i$ increased, the stimulation increased with apparent $EC_{50}$ of approximately 500 μM. The stimulatory effect of $PP_i$ was only observed when added to the cytosolic aspect of the membrane patch; external addition of 5 mM $PP_i$ did not alter currents from cells studied in the whole-cell configuration (n=4).

To determine how $PP_i$ stimulated CFTR currents, membrane patches that contained only a single active channel were studied. When 5 mM $PP_i$ was added to the cytosolic surface of the membrane patch in the presence of 0.3 mM ATP and 75 nM PKA several traces were produced. Examination of the traces suggest four things. First, $PP_i$ did not increase Cl$^-$ current by changing the amplitude of current flowing through a single c channel. In eight experiments, current amplitude was 0.90±0.05 pA before and 0.91±0.02 pA after addition of $PP_i$ (p=0.812). Second, it is apparent that the increase in total current is due to an increase in the probability that single channels are in the open state ($P_o$). Third, it appears that the increased $P_o$ is at least in part caused by an increase in the duration of bursts of activity. (Note that a burst is defined as the time in which the channel is open with only brief flickers to the closed state. Bursts are delimited by long closures of greater than 20 ms). Fourth, $PP_i$ appeared to decrease the duration of the long closed states between bursts of activity. $PP_i$ increased $P_o$ from 0.39±0.021 to 0.81±0.03 (n=8, p<0.001) and increased mean burst duration from 175±6 ms to 1568±219 ms (n=8, p<0.001).

Figure 1A:
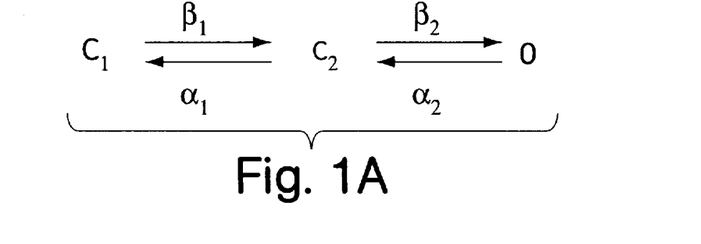
Figure 1B:
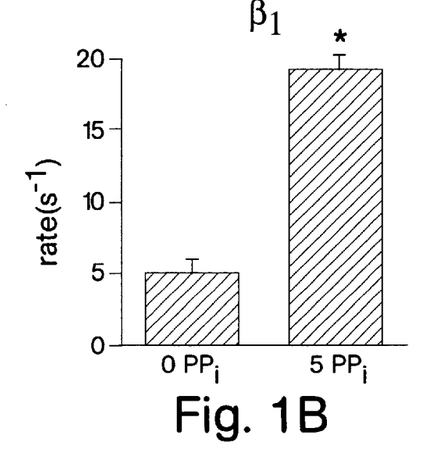
Figure 1C:
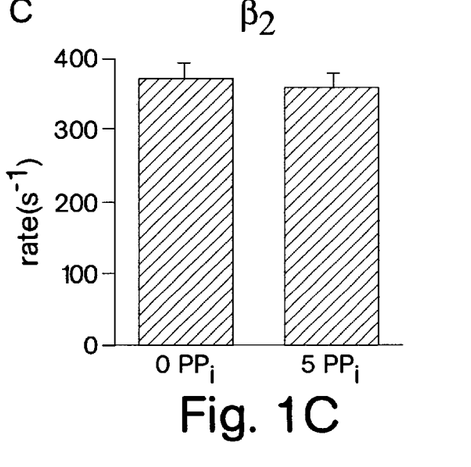
Figure 1D:
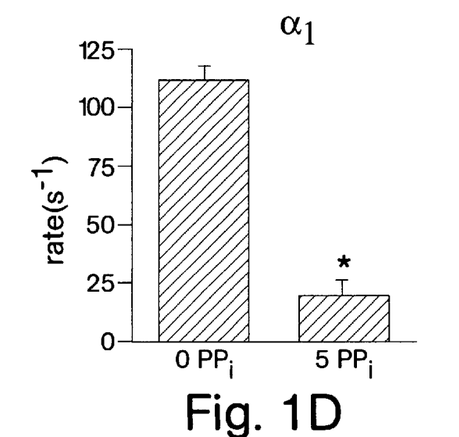
Figure 1E:
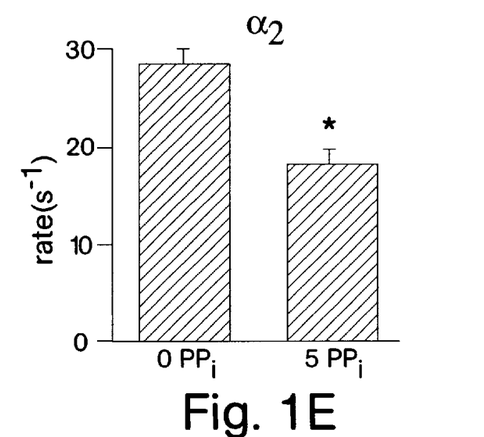

To provide more insight into the mechanism by which $PP_i$ stimulated CFTR, kinetic modeling was performed on the data from four patches which contained only a single channel. It has been previously shown that the activity of single phosphorylated CFTR channels can be described by a linear three state model (Winter, M. C. et al. (1994) *Biophys. J.* 66:1398–1403), and this model has been used to describe how ATP, ADP, and inorganic phosphate alter the rate constants which describe transitions between states (Carson, M. R. et al., 1994 *Biophys. J* (In Press); Winter, M. C. et al., 1994 *Biophys. J.* 66:1398–1403). As shown in FIG. 1A, $C_1$ represents the long closed state between bursts of openings and C2←—→O represents the bursting state, in which several channel openings (O) are separated by brief, flickery closures (C2), before the channel returns to the longer closed state (C1). The rate constants ($\beta_1$, $\beta_2$, $\alpha_1$, and $\alpha_2$) describe the rate of transition between each state.

FIG. 1B–1E describe the average values of the rate constant in the presence and absence of 5 mM $PP_i$, $PP_i$ produced large changes in both $\beta_1$ and $\alpha_1$, a smaller decrease in $\alpha_2$, and did not alter $\beta_2$. These results suggest that $PP_i$ affects more than one step in channel gating. The increase in burst duration is caused principally by a six-fold decrease in $\alpha_1$. $\alpha_1$ is a major determinant of burst duration because it defines the rate at which the channel leaves the bursting mode (i.e. leaves $C_2$, the closed state within a burst). The duration of bursts can also be affected by $\beta_2$ and $\alpha_2$, the transition rates within a burst. $PP_i$ did not alter $\alpha_2$, but decreased $\alpha_2$ by 37%. However, because $\alpha_2$ is one tenth the magnitude of $\beta_2$, the decrease in α2 produced less than a 5% change in $P_o$ within a burst (n=4, not significantly different). Thus the decrease in α2 had a minimal effect on net channel activity.

In addition to increasing burst duration, $PP_i$ also increased $\beta_1$, the rate of transition from the long closed state ($C_1$) to the bursting state ($C_2$←—→O), suggesting that $PP_i$ functioned as a channel opener. Interestingly, β1 is the only rate constant which is affected by ATP and ADP (Winter, M. C. et al. (1994) *Biophys. J.* 66:1398–1403). In other systems, $PP_i$ binding to NBDs can mimic some aspects of ATP binding. These data suggest that $PP_i$ may potentiate channel activity by interacting with CFTR at the one or both NBDs and may produce effects similar to those that occur upon ATP binding.

Together, the single channel analysis and kinetic modeling data show that in the presence of ATP, $PP_i$ had two primary effects on CFTR: first, $PP_i$ acted as a channel opener, and second, $PP_i$ prevented channel closure by prolonging the burst state.

(ii) Pyrophosphate Increases 8-$N_3$ATP Binding

One effect of $PP_i$ was to increase the rate at which channels opened. It has been previously suggested that ATP binding and hydrolysis are necessary for the channel to open. Therefore the possibility that $PP_i$ might alter the binding of ATP to CTFR was tested by examining the effect of 5 mM $PP_i$ on 8-$N_3$ATP photolabeling of membrane-associated CFTR in Sf9 cells. Previous studies showed that CFTR was labeled in a specific and saturable way by 8-$N_3$ATP, that 8-$N_3$ATP supported channel function, and that ATP competed with 8-$N_3$ATP (Travis, S. M. et al. (1993) *J. Biol. Chem.* 268:15336–15339), suggesting that 8-$N_3$ATP binding is an appropriate assay of the functional ATP binding sites in CFTR.

In these experiments, $PP_i$ produced a concentration-dependent increase in 8-$N_3$ATP labeling of CFTR, suggesting that $PP_i$ alters nucleotide binding kinetics. Since the photolabeling reaction was performed over a 60 s period, increased labeling of CFTR by $PP_i$ could be due to an increase in the rate of nucleotide binding to, and/or a decrease in the rate of nucleotide release from, one or both of the NBDs. Thus, $PP_i$ appears to increase the amount of ATP bound to CFTR.

(iii) Nonhydrolyzable $PP_i$ Analogs Stimulate CFTR Channel Activity

Because it has been proposed that hydrolysis of ATP is necessary for channel activity (Anderson, M. P. and Welsh, M. J. (1992) *Science* 257:1701–1704, Hwang, T-C. et al. (1994) *Proc Natl Acad Sci* 91:4698–4702, Anderson, M. P. et al. (1991) *Cell* 67:775–784), whether $PP_i$ may stimulate channel activity was considered by providing a nonhydrolyzable substrate. To determine if hydrolysis of $PP_i$ was necessary for the observed increase in channel activity or burst duration, the effect of the nonhydrolyzable $PP_i$ analogs imidodiphosphate (PNP), methylenediphosphonic acid (PCP), and etidronate disodium, which is a drug used clinically for treatment of hypercalcemia, was assessed (Fleisch, H., (1991) *Drugs* 42:919–944). Experiments were carried out in which the effects of PCP, PNP and etidronate were examined. Experiments were carried out in two separate excised membrane patches from C127s cells which contained only a single active channel. For all interventions 75 nM PKA and 0.3 mM ATP were present on the cytosolic surface and the $PP_i$ analogs were added at a concentration of 5 mM. These experiments showed that like $PP_i$, PCP, PNP, and etidronate prolonged bursts of activity. However, the prolonged bursts generated by these compounds were less frequent than were observed with $PP_i$, suggesting that they were less potent.

The effects of these agents on $P_o$ and average burst duration were also studied. All three nonhydrolyzable analogs altered channel activity. The effects of PCP, however, did not achieve statistical significance, suggesting that small differences between compounds, such as the electronegativity and/or angle of the bridging group, can produce a large difference in the ability to stimulate the channel. This is similar to the finding that AMP-PNP, a nonhydrolyzable ATP analog with a structure very similar to ATP (Yount, R. G., et al. (1971) *Biochem* 10:2484–2489), has a binding affinity one twentieth that of ATP (Travis, S. M. et al. (1993) *J. Biol. Chem.* 268:15336–15339). Although these data do not rule out the possibility that hydrolysis of $PP_i$ may occur, they suggest that hydrolysis of $PP_i$ is not necessary for stimulation of the channel activity or prolongation of burst duration.

The ability of $PP_i$ to potently stimulate CFTR channel activity suggested that $PP_i$ or a more stable nonhydrolyzable $PP_i$ analog might be a useful pharmacological agent to stimulate poorly functional CFTR channels that are associated with disease. To support a possible pharmacological approach, three criteria must be met. First, $PP_i$ must stimulate CFTR channels which contain CF-associated mutations. Second, $PP_i$ or an analog must be able to stimulate endogenous CFTR in the apical membrane of epithelia. And third, since stimulation occurs from the cytoplasmic aspect, $PP_i$ or an analog must be able to gain access to the interior of the cell. To address the first two issues, we performed the following studies.

(iv) $PP_i$ Stimulates CFTR Containing CF-associated Mutations

The effect of $PP_i$ on CFTR containing the CF-associated mutations ΔF508, R117H, and G551S was examined. These mutations were studied because they occur in different regions of the protein and have different mechanisms of dysfunction. CFTR-ΔF508, the most common CF causing mutation (Cutting, G. R. et al. (1990) *Nature* 346:366–369; Kerem, B-S et al. (1990) *Proc. Nati. Acad. Sci.* USA 87:8447–8451), is defectively processed and fails to traffic to the plasma membrane. In addition to the processing defect, the function of CFTR-ΔF508 is decreased as indicated by a reduced $P_o$ (Dalemans, W. et al. (1991) *Nature* 354:526–528; Sheppard, D. N. et al. (1993) *Nature* 362:160–164). G551S, a mutation in NBD1, is correctly processed but has altered ATP-dependent channel regulation resulting in a reduced $P_o$ (Anderson, M. P. and Welsh, M. J. (1992) *Science* 257:1701–1704). R117H, which contains a mutation in the membrane-spanning domain, is also correctly processed, but has altered ion conducting properties producing an overall decrease in function (Sheppard, D. N. et al. (1993) *Nature* 362:160–164).

Experiments were carried out in which a patch containing two CFTR-ΔF508 channels was used to study effects of PPi administration. In the presence of 75 nM PKA and 0.3 mM ATP, channel openings appear qualitatively similar to those of wild-type CFTR, except that both $P_o$ and burst duration are less than wild-type. Addition of 5 mM $PP_i$ stimulated ΔF508 activity three-fold (n=5). $P_o$ increased three-fold (from 0.07±0.01 to 0.21±0.022), and average burst duration increased eight-fold (from 125±19 ms to 1023±330 ms) (n=3). A similar stimulation of channel activity was observed when 1 mM $PP_i$ was added to CFTR-R117H and CFTR-G551S.

(v) Pyrophosphate Stimulates Apical Membrane Cl⁻ Currents

To learn whether $PP_i$ can stimulate endogenous CFTR in the apical membrane of epithelia, the effect of $PP_i$ was measured on permeabilized T-84 intestinal epithelial monolayers. T-84 intestinal epithelial cells grow as a polarized epithelium on permeable supports and express CFTR in their apical membrane (Madara, J. L. et al. (1987) *Gastroenterology* 92:1133–1145, Denning, G. M. et al. (1992) *J. Clin Invest* 89:339–349) Because $PP_i$ is hydrophilic and membrane impermeant, the basolateral membrane was permeabilized with S. aureus α-toxin (100 μg/ml) to provide access of small molecules, such as cAMP and $PP_i$, to the cell interior (Ostedgaard, L. S. et al. (1992) *Am. J. Physiol.* 263:L104–L112). Basolateral solutions contained 1 mM ATP. Permeabilizing the basolateral membrane also allowed for current flow to be measured across the apical membrane in the absence of the basolateral membrane barrier.

After permeabilization, the baseline Cl⁻ current was small suggesting that in the absence of cAMP, the apical membrane was relatively impermeable to Cl⁻. As previously reported, addition of cAMP to the basolateral bathing solution stimulated Cl⁻ current (Ostedgaard, L. S. et al. (1992) *Am. J. Physiol.* 263:L104–L112). Subsequent addition of either 1 or 5 mM $PP_i$ to the basolateral bathing solution produced a further increase in current.

Although $PP_i$ can function as a nonspecific phosphatase inhibitor, and CFTR channel activity is regulated in part by phosphorylation (Berger, H. A. et al. (1992) *J. Biol Chem* 268:2037–2047; Berger, H. A. et al. (1994) *Jap J Phsiol* (in press)), it is unlikely that $PP_i$ stimulated the apical membrane Cl⁻ current by acting as a nonspecific phosphatase inhibitor because removal of cAMP in the continued presence of $PP_i$ decreased current to baseline levels within 3 min. This rate is similar to that observed in the absence of $PP_i$. If the effect of $PP_i$ was in part due to phosphatase inhibition, it would be expect for the current to be maintained after removal of cAMP.

In other experiments, addition of 1 or 5 mM $PP_i$ to permeabilized monolayers in the absence of cAMP did not increase current above baseline levels. This result suggests that $PP_i$ only stimulates apical Cl⁻ current in the presence of cAMP, a result consistent with the findings that $PP_i$ only stimulated phosphorylated CFTR Cl⁻ channels in excised membrane patches.

(vi) Mechanism of Action

Although not wishing to be bound by theory, the results obtained in the above-described experiments support the following possible mechanism of action of $PP_i$ or its non-hydrolyzable analogs on stimulation of wild-type or mutant CFTR Cl⁻ channels.

$PP_i$ binds to the glycine-rich loop in a number of proteins that contain nucleotide binding domains (Peinnequin, A. et al. (1992) *Biochem* 31:2088–2092; Michel, L. et al. (1989) *Biochem* 28:10022–10028; Issartel, J. P., et al. (1987) *J. Biol. Chem* 262 28:13538–13544; Thomas, P. J. et al. (1992) *J. Biol. Chem.* 267:5727–5730; Bartels, E. M. et al. (1993) *Biochim Biophys. Acta* 1157:63–73; and Greene, L. E. et al. (1980) *J. Biol Chem* 255:543–548). Data described in Example I below show that $PP_i$ also interacted with CFTR and reversibly stimulated the activity of phosphorylated channels. $PP_i$ was not able to stimulate activity on its own; it required the simultaneous presence of ATP. The ability of non-hydrolyzable analogs such as PNP, PCP, and etidronate to mimic the effect of $PP_i$ indicates that hydrolysis of $PP_i$ is not required for stimulation.

The data show that $PP_i$ increased the channel open probability predominantly by affecting the rate of two transitions. $PP_i$ increased $β_1$, the rate at which the channel leaves the long closed state and enters a burst of activity. $PP_i$ also decreased $α_i$, the rate at which the channel leaves a burst and returns to the long closed state. Although either an increase in $β_1$ or a decrease in $α_1$ will increase $P_o$, previous work indicates the $β_1$ and $α_1$ transitions are distinct steps that are not directly related (Winter, M. C. et al. (1994) *Biophys J* 66:1398–1403).

First, $PP_i$ binding itself cannot open the channel because $PP_i$ did not support channel activity alone; the stimulatory effect of $PP_i$ required the presence of ATP. This observation is consistent with previous data suggesting that ATP binding and hydrolysis is required to open the channel (Hwang, T.-C et al. (1994) *Proc Natl Acad Sci* 91:4698–4702; Baukrowitz, T. et al. (1994) *Neuron* 12:473–482; and Anderson, M. P. et al. (1991) *Cell* 67:775–784). Second, the findings that $PP_i$ stimulated a rate ($β_1$) that is controlled by ATP, and that $PP_i$ increased the binding of the ATP analog $8-N_3ATP$ indicate that the effect of $PP_i$ is allosteric. It was concluded that $PP_i$ binds to a site in CFTR other than the site at which an ATP interaction directly opens the channel. When $PP_i$ binds to the allosteric site, it facilitates binding (and perhaps hydrolysis)

of ATP, increasing the rate at which the channel opens. These data are the first direct evidence for a compound having an allosteric effect on CFTR gating activity.

Previous work indicated that mutations expected to reduce the rate of hydrolysis at NBD2 increased the duration of bursts. Non-hydrolyzable analogs of ATP also prolonged the duration of bursts (Baukrowitz, T. et al. (1994) *Neuron* 12:473–482; Gunderson, K. L. et al. (1994) *J. Biol. Chem* 269:19349–19353) as does $PP_i$ when added to CFTR studied in artificial lipid bilayers (Gunderson, K. L. et al. (1994) *J. Biol. Chem* 269:19349–19353)). These data suggested that the rate of hydrolysis at NBD2 is a primary factor in terminating bursts and thus in determining their duration. The data suggests that $PP_i$ prolongs the duration of bursts by binding to $NBD_2$ which stabilizes the bursting state; because $PP_i$ is not hydrolyzed, the interaction is prolonged, the termination of a burst is delayed, and $\alpha_1$ decreases.

Figure 2A:
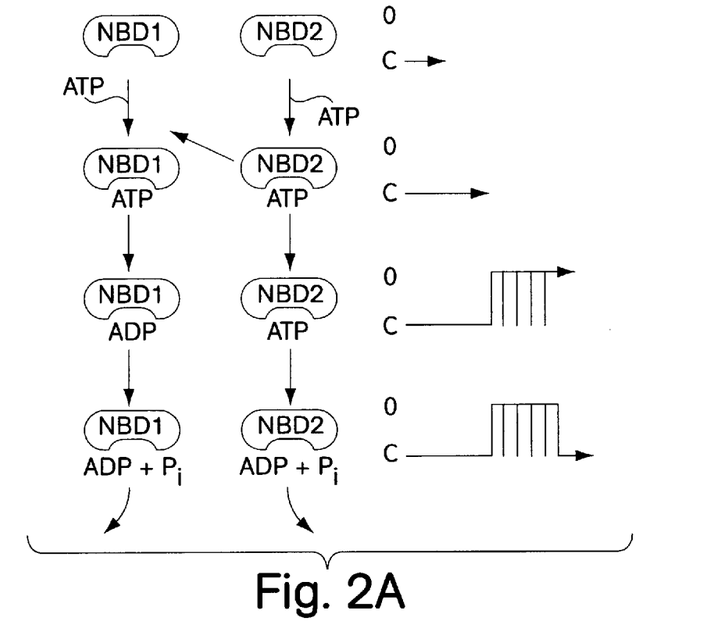

A model of how events at NBD1 and NBD2 give rise to the opening and closing of phosphorylated channels is shown in FIG. 2A, where vertical columns represent events occurring at NBD1, at NBD2, and the corresponding channel activity. A key feature of this model is that the two NBDs have different functions. In the absence of ATP the channel is closed (top of FIG. 2A). Binding of ATP to NBD2 allosterically regulates events at NBD1, including a step leading to channel opening, which may be ATP binding and/or hydrolysis. This is shown in the model as an arrow from NBD2 to NBD1. Once ATP has bound to both NBDs, ATP hydrolysis at NBD1 opens the channel to the bursting state. ATP bound to NBD2 stabilizes the bursting state by allosterically stabilizing the open state conformation at NBD1. Eventually, hydrolysis of ATP at NBD2 occurs which destabilizes the bursting state, and the channel closes from the bursting state to the long closed state.

The fact that PPi has been shown to bind to NBD of CFTR provides a strong precedent for $PP_i$ binding to the NBDs of other ABC proteins, where it can mimic some aspects of ATP binding. $PP_i$ most likely exerts its effects by binding to NBD2. Previous study of CFTR mutants has shown that NBD2 appears to regulate the duration of burst. In addition, NBD2 mutations altered the rate at which the channel opens. Both of these processes are influenced by $PP_i$. Moreover, it has been shown that addition of non-hydrolyzable ATP analogs can prolong the duration of bursts, an effect attributed to NBD2, suggesting that the rate of hydrolysis regulates the duration of bursts.

Figure 2B:
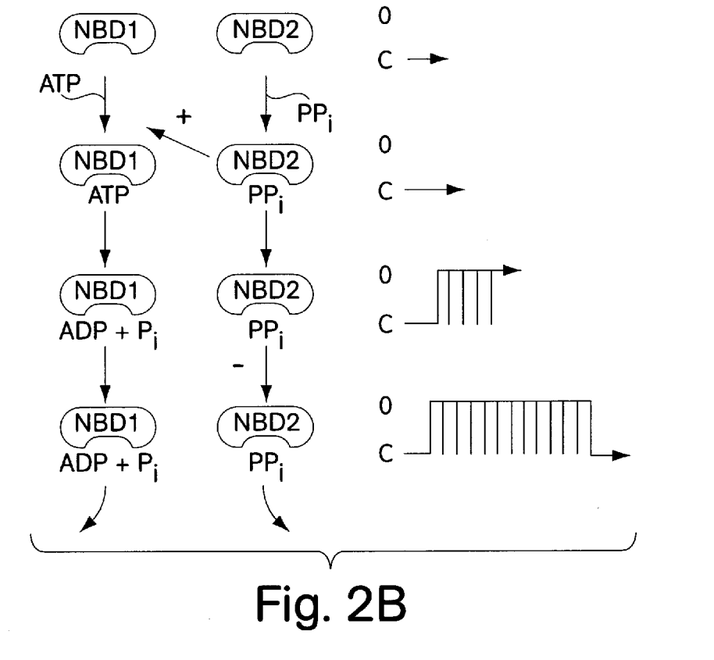

In the model appearing in FIG. 2B, it is shown that $PP_i$ can substitute for ATP in binding to NBD2. When $PP_i$ binds, it mimics the effect of ATP binding, allosterically increasing the binding (and perhaps hydrolysis) of ATP at NBD1 (indicated by the "+" in FIG. 2B). Hydrolysis of ATP at NBD1 then opens channel to the bursting state. While $PP_i$ remains bound to NBD2, the bursting state is stabilized, as if ATP were present (third panel from top in FIG. 2B). Unlike ATP, however, $PP_i$ is not hydrolyzed and the channel remains stabilized in the bursting state for a prolonged period (indicated by "−" in FIG. 2B). In this case, termination of the burst may occur only when $PP_i$ has dissociated from NBD2.

Why $PP_i$ would show preferential binding to NBD2 is not known, but the two NBDs do have significantly different amino acid sequences, and there is substantial precedent for nucleotide-binding sites that show preference between different analogs and $PP_i$. The finding that 5 mM $PP_i$ plus 0.3 mM ATP (Example 1) opens the channel more rapidly than 0.3 mM ATP alone and the observation that $PP_i$ stimulates binding of 30 mM 8-$N_3$ATP may be due to the high concentration of $PP_i$ relative to ATP. Perhaps the binding affinity or steric constraints of NBD2 are more favorable for $PP_i$ binding.

Thus, it is possible that the $PP_i$ interacts primarily with NBD2 and in so doing it alters two functions of NBD2: a) it has an allosteric effect on NBD1, enhancing binding and/or hydrolysis of ATP and b) because it is not hydrolyzed it stabilizes the bursting state preventing channel closure.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A pharmaceutical composition comprising an aerosolized inorganic pyrophosphate (PPi) in a form that renders the PPi accessible to ATP-binding cassette (ABC) proteins when administered by inhalation to a subject in vivo.

2. The pharmaceutical composition of claim 1, wherein said inorganic pyrophosphate is non-hydrolyzable.

3. The pharmaceutical composition of claim 2, wherein said non-hydrolyzable inorganic pyrophosphate is selected from the group consisting of etidronate disodium, immidophosphate (PNP) and methylenediphosphonic acid (PCP).

4. The pharmaceutical composition of claim 1, comprising a delivery vehicle selected from the group consisting of a detergent, membrane vesicle, liposome, virosome and microsome.

5. The pharmaceutical composition of claim 1, wherein said composition is chemically modified to increase hydrophobicity and allow partitioning through the lipid membrane of the cells.

6. The pharmaceutical composition of claim 5, wherein at least one phosphoester has been added to the charged oxygens of the inorganic pyrophosphate.

7. The pharmaceutical composition of claim 1 of a dosage effective to increase the activity of an ATP-binding cassette (ABC) protein.

8. The pharmaceutical composition of claim 7, wherein said ABC protein is a mammalian ABC protein.

9. The pharmaceutical composition of claim 8, wherein said mammalian ABC protein is selected from the group consisting of the cystic fibrosis conductance transmembrane regulator protein (CFTR), P-glycoprotein, peroxisomal membrane protein (PMP70), and MHC-linked (TAP) transport protein.

10. The pharmaceutical composition of claim 8, wherein said mammalian ABC protein is the cystic fibrosis conductance transmembrane regulator protein (CFTR).

11. The pharmaceutical composition of claim 1, wherein said PPi is administered at a dosage that is effective to increase the activity of an ABC protein.

* * * * *

UNITED STATES PATENT AND TRADEMARK OFFICE
CERTIFICATE OF CORRECTION

PATENT NO. : 5,958,907
DATED : September 28, 1999
INVENTOR(S) : Michael J. Welsh It is certified that error appears in the above-identified patent and that said Letters Patent is hereby corrected as shown below:

Column 1, line 5, add the following:

This invention was supported in part by NIH grant HL-42385, the government has certain rights to the invention--.

Signed and Sealed this

Twenty-fifth Day of April, 2000

Attest:

Q. TODD DICKINSON

Attesting Officer

Director of Patents and Trademarks